(12) United States Patent
Speier

(10) Patent No.: US 11,033,198 B2
(45) Date of Patent: Jun. 15, 2021

(54) METHOD AND MAGNETIC RESONANCE APPARATUS FOR PERFORMING ELECTRICAL IMPEDANCE TOMOGRAPHY WITH THE AID OF AN MR SYSTEM

(71) Applicant: Siemens Healthcare GmbH, Erlangen (DE)

(72) Inventor: Peter Speier, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 154 days.

(21) Appl. No.: 16/367,796

(22) Filed: Mar. 28, 2019

(65) Prior Publication Data

US 2019/0298217 A1 Oct. 3, 2019

(30) Foreign Application Priority Data

Mar. 28, 2018 (EP) .................................. 18164693

(51) Int. Cl.
*G01R 33/483* (2006.01)
*A61B 5/0536* (2021.01)
(Continued)

(52) U.S. Cl.
CPC ............ *A61B 5/0536* (2013.01); *A61B 5/055* (2013.01); *G01R 33/4808* (2013.01);
(Continued)

(58) Field of Classification Search
CPC ....... A61B 5/053; A61B 5/055; A61B 5/0035; A61B 5/0536; G01R 33/56;
(Continued)

(56) References Cited

U.S. PATENT DOCUMENTS 6,397,095 B1  5/2002  Eyuboglu et al.
7,511,492 B2  3/2009  Sodickson et al.
(Continued)

FOREIGN PATENT DOCUMENTS

DE  102015224158 A1  6/2017
DE  102015224162 A1  6/2017
(Continued)

OTHER PUBLICATIONS

Zhang et al. Magnetic-Resonance-Based Electrical Properties Tomography: A Review, IEEE Reviews in Biomedical Engineering, vol. 7, 2014, pp. 87-96 (Year: 2014).*
(Continued)

*Primary Examiner* — Melissa J Koval
*Assistant Examiner* — Courtney G McDonnough
(74) *Attorney, Agent, or Firm* — Schiff Hardin LLP

(57) ABSTRACT

The present invention relates to a method for performing electrical impedance tomography (EIT) by an MR system, wherein during the MR measurement continuous RF signals for an EIT measurement are emitted by at least one RF coil of the MR system, and continuous RF signals modulated by the object undergoing examination are received by the receiving coils of the MR system. An image of the object undergoing examination is determined, based on the modulated continuous RF signals, by an EIT technique.

20 Claims, 2 Drawing Sheets

(51) Int. Cl.
*A61B 5/055* (2006.01)
*G01R 33/56* (2006.01)
*G01R 33/48* (2006.01)
*A61B 5/00* (2006.01)
*G01R 33/36* (2006.01)
*G01R 33/385* (2006.01)
*G01R 33/24* (2006.01)
*G01R 33/565* (2006.01)

(52) U.S. Cl.
CPC ............ *G01R 33/56* (2013.01); *A61B 5/0035* (2013.01); *G01R 33/246* (2013.01); *G01R 33/3628* (2013.01); *G01R 33/385* (2013.01); *G01R 33/56509* (2013.01)

(58) Field of Classification Search
CPC .............. G01R 33/4808; G01R 33/246; G01R 33/3628; G01R 33/385; G01R 33/56509
USPC ........................................................ 324/309
See application file for complete search history.

(56) References Cited

U.S. PATENT DOCUMENTS

| 7,795,870 B2 | 9/2010 | Sodickson et al. |
| 8,929,970 B2 | 1/2015 | Wollin |
| 2013/0072780 A1 | 3/2013 | Espy et al. |
| 2017/0160364 A1 | 6/2017 | Fenchel et al. |
| 2017/0160367 A1 | 6/2017 | Schroter et al. |
| 2017/0303991 A1 | 10/2017 | Rubinsky et al. |
| 2018/0045801 A1 | 2/2018 | Speier et al. |

FOREIGN PATENT DOCUMENTS

| DE | 102015224162 B4 | 11/2017 |
| DE | 102016215044 A1 | 2/2018 |

OTHER PUBLICATIONS

Woo et al. Magnetic resonance electrical impedance tomography (MREIT) for high resolution conductivity imaging, Physiol. Meas. 29 (2008) R1-R26 (Year: 2008).*

"PulmoVista500", in: http://www.draeger.com/sites/de_de/Pages/Hospital/PulmoVista-500.aspx, and English language translation.

Wikipedia "Elektrische Impedanz-Tomografie (EIT)" https://de.wikipedia.org/wiki/Elektrische_impedanz-Tomografie, vom Jan. 24, 2018, English language translation.

Schröder, Lea "Information Content of a Novel MR Navigator Relating to Physiological Activities" Master's Thesis in Medical Engineering; Friedrich-Alexander—University Erlangen—Nürnberg; Dec. 2015.

Tittman, Jay "Geophysical Well Logging" Methods of Experimental Physics, vol. 24, Geophysics, 1986, ISBN.

* cited by examiner

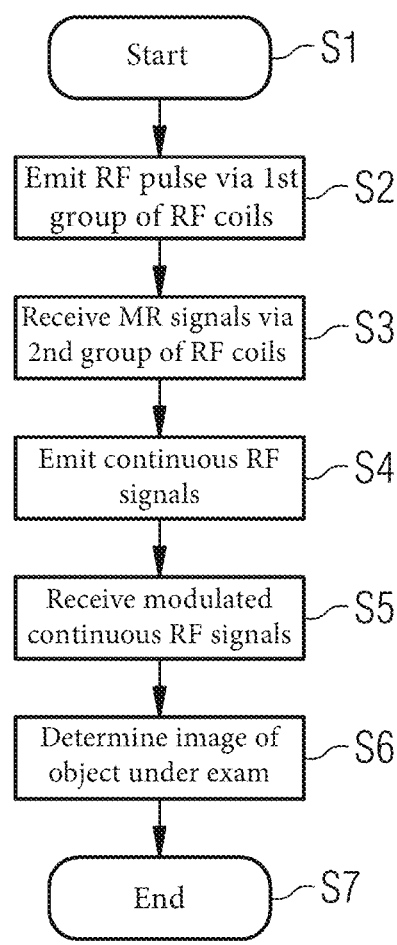

METHOD AND MAGNETIC RESONANCE APPARATUS FOR PERFORMING ELECTRICAL IMPEDANCE TOMOGRAPHY WITH THE AID OF AN MR SYSTEM

BACKGROUND OF THE INVENTION

Field of the Invention

The present invention concerns a method for performing electrical impedance tomography with the use of a magnetic resonance (MR) system. The present invention also concerns an MR apparatus, and a non-transitory, computer-readable data storage medium encoded with programming instructions, that implements such a method.

Description of the Prior Art

Electrical impedance tomography (EIT) is a non-invasive imaging method that is based on measurements of electrical conductivities in the human body. This measuring method is based on the fact that the electrical conductivities of biological tissues differ, depending on their nature (absolute EIT) and/or functional condition (functional or relative EIT). In addition to the approaches of absolute and functional EIT, in which alternating currents of a single frequency are usually utilized, it is also possible to supply alternating currents of different wavelengths, as known for example from the Wikipedia article "Elektrische Impedanz-Tomografie", retrieved on Feb. 27, 2018 from [https://de.wikipedia.org/wiki/Elektrische_Impedanz-Tomografie].

Using a special technique of EIT, multiple surface electrodes are positioned on an object, wherein alternating electrical currents flow between two respective electrodes while, with the use of the other electrodes, the electrical potential is simultaneously recorded. The detected surface currents, or the detected electrical potential, depend on the distribution of current in the object, and this distribution is influenced by the electrical impedance distribution in the objects. The goal is to calculate a spatially encoded impedance distribution that generates the measured surface currents. However, this inversion problem is ill-posed, and can be solved with only the use of severe constraints on the geometry and structure of the object.

EIT has been used since the 1930s in oil extraction and has become established as a basic source of information for commercial in-situ formation evaluation. Most geometrical basic models have infinitely wide, electrically homogeneous formation layers aligned at a right angle to the borehole. Currents are supplied to the formation by electrodes that are in contact with the formation or, in the case of high frequencies, with the use of antenna arrangements by induction, as known for example from the publication "Geophysical Well Logging" by Jay Tittman in Academic Press 1986, ISBN 0-12-691390-0, Chapters 2.7 and 3.1.

EIT methods are also applied in the case of medical problems such as perfusion and mammography; a commercial medical application here is, for example, the spatially encoded representation of a patient's pulmonary ventilation with the use of a sensor belt placed around the upper body.

U.S. Pat. No. 8,929,970 B2 discloses a method for detecting and evaluating spatially ordered pathological changes in a person under medical examination by observing phase changes in MRI spin signals that are caused by time-variable differences in the electrical potential in Faraday shields placed outside the patient. In contrast to EIT, in this method the spatial encoding is with an MRI measurement. An example application is the identification of breast pathology. The method described in U.S. Pat. No. 8,929,970 B2 differs from the method according to the invention in that the induced currents described in U.S. Pat. No. 8,929,970 B2 are so large that they generate local magnetic fields that are strong enough to generate measurable changes in the local spin dynamic. These changes are then analyzed in order to derive therefrom local electrical properties.

U.S. Pat. No. 7,511,492 B2 and U.S. Pat. No. 7,795,870 B2 disclose a radio-frequency impedance imaging method that is integrated into an MRI measurement (RF impedance mapping, RFIM), a variant of EIT that uses inductive coupling instead of galvanic coupling for the MR frequency. The interaction of MRI with the induced currents is utilized to stabilize the model inversion. B1 mapping is described as a possible application. The described scanner combines MR with RFIM by using the MR receiving coils for the electrical measurement, but additional emitting and receiving capabilities are required i.e., additional circuits for all the local coils, in order to measure and monitor their impedance. Further, only the RF coils are used together but not the RF generating and receiving system. For this reason, the MR measurement has to be adapted such that the RFIM measurement can be interpolated between the emission of MR RF pulses and the receiving of MR signals, so EIT measurements must be performed to alternate in time with the MR measurements. Since an MR measuring sequence includes multiple excitations and outputs, this is called an interweaving of events i.e., methods are interleaved with one another. However, this does not enable simultaneous—in other words temporally parallel—MR and RFIM measurements that are independent of one another, since the coils are connected to separate electronic systems during the two measurements.

DE 102015224162 A1, DE 102015224158 A1, DE 102015224162 B4, DE 102016215044 A1 and the Master's thesis "Informationsgehalt eines neuartigen MR-Navigators in Bezug auf physiologische Vorgänge [*Information content of a novel MR navigator relating to physiological procedures*]" by Lea Schröder, Friedrich-Alexander-Universität Erlangen-Nürnberg, 2015, disclose a method for determining motion, in particular respiratory motion and cardiac motion, using a pilot tone (PT) signal. The PT signal, which is a radio-frequency signal, is generated continuously by a PT emitting coil and detected together with the MR signal. The emitted pilot tone signal undergoes a modulation caused by the examination object, in particular a modulation of the phase and amplitude of the PT signal. Since the phase of the pilot tone is known, the point in time at which the MR signal is detected can be derived from this knowledge.

To summarize, in the prior art special EIT devices are needed to convert EIT measurements. These include signal generators, signal application hardware (electrodes), signal receiving hardware (electrodes), signal analyzing hardware (amplifiers, detectors), and computers for signal processing and model inversion. In addition, restrictions on models must be generated and fed into the reconstruction. These may be produced from general anatomic models, or rather, with individual optimization, from separate examinations using high-resolution imaging methods such as CT, MR, or comparable examination methods.

There is thus a need for an improved method for electrical impedance tomography that can be performed more simply and with shorter examination times. There is furthermore a need to improve the quality and efficiency of existing EIT techniques in order to stabilize existing EIT applications and open up new applications.

SUMMARY OF THE INVENTION

According to a first aspect of the invention, a method for performing electrical impedance tomography (EIT) is provided that is performed by an MR system having multiple RF coils. The MR system may be an MR system with integrated pilot tone navigation.

In a first step, an RF pulse is emitted using a first group of RF coils, for the purpose of exciting nuclear spins in the object undergoing examination. In a further step, MR signals from the object undergoing examination, based on the RF pulse, are received by a second group of RF coils. In an additional step, continuous RF signals having amplitudes in the same order of magnitude as the amplitudes of the MR signals are emitted by at least one RF coil.

In a further step, modulated continuous RF signals from the object undergoing examination in response to the continuous RF signals are received by the second group of RF coils. The continuous RF signals undergo a modulation by the object undergoing examination, in particular a modulation of the phase and/or a modulation of the amplitude. As a result, modulated continuous RF signals from the object undergoing examination are generated. In an additional step, an image of the object undergoing examination is determined on the basis of the modulated continuous RF signals. In particular, image data is determined from the modulated continuous RF signals, and the image of the object undergoing examination is based on this. In this way, the modulated continuous RF signals are evaluated such that an image of the object undergoing examination can be generated in accordance with an EIT technique. Here, emission of the continuous RF signals and receiving of the modulated continuous RF signals are performed simultaneously with receiving of the MR signals.

The amplitudes of the continuous RF signals are in the same order of magnitude as the amplitudes of the MR signals received from the object undergoing examination. In particular, they may be the same size or substantially the same size as the amplitudes of the MR signals, with the result that spin of the object undergoing examination and the MRI measurement is not affected. The MRI measurement is disrupted by excessively large amplitudes as a result of two mechanisms: on the one hand if the amplitude of the continuous RF signals is large enough to excite spin (approximately 4-6 orders of magnitude, mV->kV); on the other if it is large enough to disrupt MRI signal detection by saturation or loss of the signal fidelity of the receiver. The amplitudes of the MR signals can fluctuate by several orders of magnitude, depending on the object and the measuring sequence. For this reason, it may be advantageous to specify a "maximum detectable MR signal" and then to select the order of magnitude of the PT signal to be less than or equal to this signal, for example between the same size and a factor of 100 (2 orders of magnitude, 40 dB) smaller. Excessively small PT amplitudes have the disadvantage that the SNR of the PT measurement becomes smaller.

The amplitudes may lie in the mV range, whereas the amplitudes of the RF pulse lie in the kW range. The comparable size of the amplitudes allows the possibility that the spin of the object undergoing examination will be affected by the continuous RF signals and hence that the MR measurement will be disrupted to be eliminated. To summarize, the RF signals have a negligible effect on the spin dynamic as a result of the small-amplitude currents that are required in order to remain within the high-signal-fidelity, unsaturated range of the MR receivers. As a result, the method according to the invention can perform an EIT measurement independently of the MR measurement—that is to say without adapting the MR measurement—independently and simultaneously.

The hardware for receiving the MR signals and the modulated continuous RF signals may have a non-linear characteristic, but this may be compensated by the software, enabling a linear evaluation of the received signals when they are combined. Furthermore, the method according to the invention receives the applied current directly after it has passed through the object, rather than detecting changes in the spin signal.

The method according to the invention does not need any additional measuring or other circuits, apart from the hardware required for the MR measurement, but receives and evaluates the RF signals by performing EIT purely using additional software. The only hardware required is one or more PT emitters of the MR system, which are already present for the MR examination—that is to say small, inexpensive RF coils, which are easy to integrate or position. In one configuration, the PT emitters may be wireless. Advantageously, the RF coils may be incorporated into a local coil of the MR system and hence into one of the RF coils that receive MR signals, and thus utilize the already present power supply and where appropriate the signal generating capability of magnetic resonance. Moreover, there is no need for separate housings or cables for PT generator coils that take this form.

In this way, a purely software solution may be provided on an MR system having integrated pilot tone navigation. This allows EIT to be commercialized even where only isolated medical applications exist, with the result that medical provision is improved for patients. The close connection with MR imaging enhances the quality of the EIT results, and has the potential to open up new applications. In particular, EIT can be performed in parallel with the MR measurement, without additional preparation of the patient. As is known from combining other modalities (CT-PET, MR-PET), this enhances the specificity of the results.

Furthermore, the continuous RF signals do not disrupt the relevant nuclear spins, since their amplitude is of comparable size with that of the MR signal, and their narrow frequency content seldom (or never) coincides with the local Larmor frequency. The required signal-to-noise ratio (SNR) of the PT measurement is ensured by a narrow-band lock-in detection in the digital range over a period which is brief by comparison with macroscopic physiological processes. The method according to the invention thus can be used to implement the RFIM method on a standard MR scanner with no or only minimal changes to the hardware.

The EIT-based characterization of tissue can be used for medical purposes. Using frequencies close to the Larmor frequency in the scanner, such as MR-RFIM, makes an additional utilization possible: EIT results can then be used for patient-specific modeling of B1 in order to support steps taken to optimize MRI, such as SAR calculations or PTx adaptations.

As a result, it becomes possible to carry out EIT imaging more quickly and more efficiently with the use of an MR system, utilizing the hardware of an MR system simultaneously with an MR measurement without affecting, or being affected by, the MR measurement. The method according to the invention requires little time or staff for an examination, and so results in improved provision for patients at lower cost than in conventional EIT methods. The method according to the invention thus enhances the quality of conventional EIT measurements and hence makes it possible to stabilize existing applications and to make new applications available by providing high-quality modeling input in real time for determining EIT images.

The frequency or frequencies of the continuous RF signals can be selected such that the resonance condition for exciting nuclear spins does not occur, and so nuclear spins are not excited in the object undergoing examination, nor is excitation of the nuclear spins affected by the RF pulse.

The frequency or frequencies of the continuous RF signals may lie outside the frequency range of the MR signals from the object undergoing examination and within a receiving range of the second group of RF coils. The continuous RF signals may comprise a single-frequency RF signal, and the continuous RF signals may comprise an RF signal of constant amplitude.

By emitting a single-frequency RF signal, in particular one with constant amplitudes and frequencies outside the resonance condition, emission can advantageously be performed simultaneously with the MR measurement. Furthermore, there are no additional requirements of the hardware of an existing MR system with pilot tone navigation. Separating the receiving frequencies of the MR measurement and the EIT measurement makes it possible to separate the respective data simply and for the measurements to have little effect on one another, and thus for there to be a reduced error rate. In this way, the modulated continuous RF signals for determining EIT image information may be received in a particularly simple way by the existing receiving coils of the MR system. The at least one RF coil that is used to emit the RF signals may be a pilot tone navigator coil that is present in the MR system. By using the already present pilot tone coil, there is no need to incorporate additional hardware into the MR system in order to perform an EIT measurement.

The at least one RF coil that is used to emit the continuous RF signals may be integrated into one of the RF coils of the second group of RF coils, and may utilize the power supply and the signal generating capability already provided there, as well as the housing and cabling.

It is possible for the at least one RF coil for emitting the continuous RF signals not to be integrated into one of the RF coils of the first or second group of RF coils and to be placed closer to the object undergoing examination than these RF coils. The at least one RF coil may be placed closer to the object undergoing examination than any of the RF coils of the first and second group of RF coils.

Because the at least one RF coil that is used to emit the continuous RF signals is not integrated into an RF coil of the MR measurement method, there is more freedom in respect of the arrangement of the at least one RF coil. The quality of the EIT measurement can be improved by arranging the at least one RF coil closer to the object undergoing examination, and in some cases also closer to certain regions of interest in the object undergoing examination, such as particular organs of a person undergoing examination. This further simplifies performing the EIT measurement method simultaneously with the MR measurement method and enhances the quality of the EIT examination.

Determining an image of the object undergoing examination may include determining a phase of the modulated continuous RF signals. Here, an absolute phase may be determined in relation to the emitted continuous RF signals. Furthermore, a relative phase change in the modulated continuous RF signals over time may be detected. Detection of the phase of the modulated continuous RF signals enables an improvement in the EIT method with no need for additional hardware to be incorporated into the MR system. In particular, there is no need to provide additional measuring circuits, configured for example to measure and monitor impedance of the RF coils of the first or second group of RF coils, in the existing MR system in order to perform the EIT measurement.

An image of the object undergoing examination may be determined using the received MR signals; in particular, as a result the additional use of information from the MR measurement enables the EIT image provided to be simpler and of higher quality.

The method may furthermore include determining a frequency range of the received MR signals from the object undergoing examination, and emission of the continuous RF signals outside the determined frequency range of the MR signals. By determining the frequency range of the received MR signals, the continuous RF signals may be emitted at frequencies that are not present in the MR signals. In particular, the continuous signals may lie approximately one MHz away from the range of the MR signals. This enables the data signals of the two imaging methods to be separated, as a result of which the EIT method can be performed, simultaneously with the MR measurement, more quickly and with fewer errors.

The continuous RF signals may be emitted by a number of RF coils i.e., the at least one RF coil that is used to emit the continuous RF signals may be a number of RF coils.

Here, the multiple RF coils may simultaneously emit different continuous RF signals that differ in respect of one or more emission properties. The emission properties can be frequency, their relative phases, amplitudes, direction of electromagnetic polarization, or signal modulation.

The multiple RF coils may emit RF signals sequentially. The emission properties may vary sequentially.

It is also possible according to the invention to sue a combination of sequentially emitting RF coils and continuous RF signals that differ with respect to their frequency, the direction of their electromagnetic polarization, or their signal modulation. As a result the multiple RF coils that emit continuous RF signals, the density of information of the EIT method is increased, and so more information and more precise information is collected, and this can be used to determine the EIT image. This enables the object undergoing examination to be imaged by the EIT method more quickly and more accurately.

At least one of the multiple RF coils can be shifted in space relative to the object undergoing examination during the EIT measuring sequence. The shift enables additional information to be measured, and enhances the quality of the EIT imaging.

The object undergoing examination can undergo a dynamic change, wherein only the variations in the modulated continuous RF signals are taken into account when the image of the object undergoing examination is determined, on the basis of the dynamic change. This allows the quantity of data of the EIT measurement data for processing to be reduced, wherein only the essential information in respect of the dynamic change of interest for the EIT imaging is taken into account. This results in a faster measurement result and enables evaluation and imaging by the EIT measurement method to be faster.

The modulated continuous RF signals may be received using RF coils from the second group of RF coils. These coils are also used, in addition to receiving EIT signals, to receive MR signals; in particular, the said signals are received in parallel or simultaneously with one another. The EIT signals—that is to say the continuous modulated RF signals—are consequently evaluated in order to determine an image of the object undergoing examination.

According to a further aspect of the invention, an MR system for performing electrical impedance tomography (EIT) on an object undergoing examination is provided. The MR system has multiple RF coils, an MR control computer and a memory. The MR control computer operates the MR apparatus in order to perform the following steps.

In a first step, an RF pulse is emitted using a first group of RF coils, for the purpose of exciting spin in the object undergoing examination. In a further step, MR signals from the object undergoing examination, based on the RF pulse, are received by a second group of RF coils. In an additional step, continuous RF signals are emitted by at least one RF coil, and these have amplitudes in the same order of magnitude as the amplitudes of the MR signals. In a further step, modulated continuous RF signals from the object undergoing examination, in response to the continuous RF signals, are received by the second group of RF coils. In particular here, the continuous RF signals undergo a modulation by the object undergoing examination, in particular a modulation of the phase and/or a modulation of the amplitude or frequency, as a result of which the modulated continuous RF signals from the object undergoing examination are generated. In an additional step, an image of the object undergoing examination is determined on the basis of the modulated continuous RF signals. In particular, image data is determined from the modulated continuous RF signals, on which the image of the object undergoing examination is based. In this way, the modulated continuous RF signals are evaluated such that an image of the object undergoing examination can be generated in accordance with an EIT technique. Here, emission of the continuous RF signals and receiving of the modulated continuous RF signals are performed simultaneously with the receiving of MR signals.

The MR system can be configured to perform the method corresponding to the further features described above when the control information is executed in the MR control unit.

For an MR system of this kind for performing electrical impedance tomography (EIT), it is possible to achieve technical effects that are comparable with the technical effects described above for the method according to the first aspect.

The present invention also encompasses a non-transitory, computer-readable data storage medium encoded with programming instructions that, when the storage medium is loaded into a control computer or computer system of a magnetic resonance apparatus, cause the computer or computer system to operate the MR apparatus so as to implement any or all embodiments of the method according to the invention, as described above.

BRIEF DESCRIPTION OF THE DRAWINGS

FIG. 2 is a flowchart with steps for performing a method for performing electrical impedance tomography (EIT) according to an exemplary embodiment of the invention.

DESCRIPTION OF THE PREFERRED EMBODIMENTS

Figure 1:
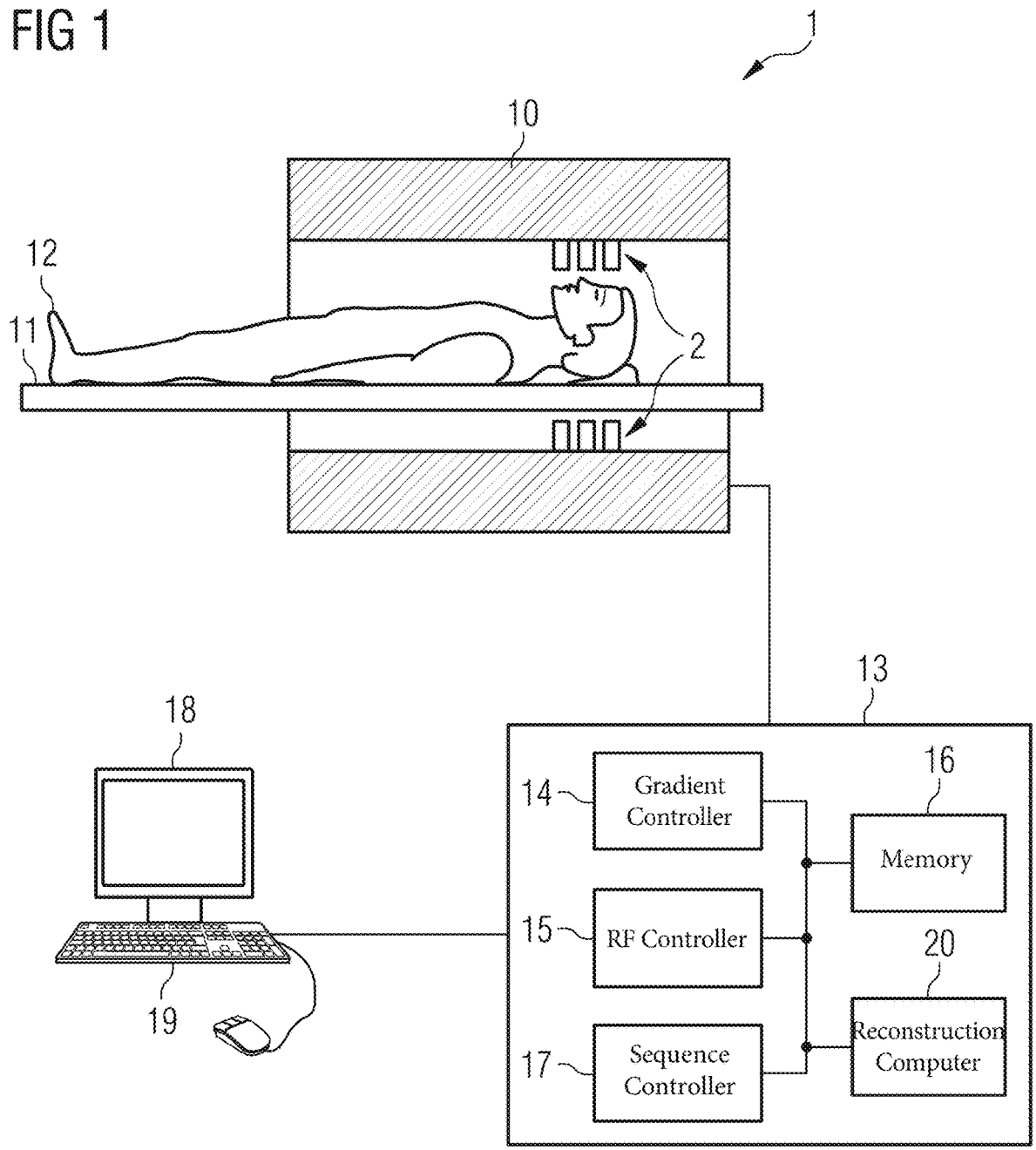
FIG. 1 schematically illustrates an MR apparatus with which a method for performing electrical impedance tomography (EIT) can be performed according to the invention.

The present invention relates to a method for performing electrical impedance tomography (EIT) with the use of an MR system.

FIG. 1 schematically shows an MR apparatus with which a method of this kind for performing electrical impedance tomography (EIT) can be performed according to the invention.

A person under examination 12, or more generally an object undergoing examination, is put inside the tunnel of the scanner 109 of the apparatus. The magnetic resonance scanner 10 has a basic field magnet that generates a basic field BO. The person undergoing examination 12, who is on a table 11, is moved into the center of the scanner 10 in order to receive spatially encoded magnetic resonance signals from the person 12. By radiating sequences of radio-frequency pulses and switching magnetic field gradients, the alignment of nuclear spins with the basic field BO is disrupted by deflecting the nuclear spins from the equilibrium position, and when the nuclear spins return to the equilibrium position, currents that are induced in receiving coils are converted to magnetic resonance (MR) signals. The general operation of creating MR images and the detection of the magnetic resonance signals are known to those skilled in the art, so a more detailed explanation is not necessary herein. Within the context of the present invention, the terms "coil", "RF coil", "MR emitting coil" or "MR receiving coil" do not typically refer to wound conductors but, in the case of MR systems, simple conductor loops.

The magnetic resonance apparatus 1 has a number of RF coils. The RF coils include a first group of RF coils, which are configured to emit at least one RF pulse for exciting nuclear spins in the object undergoing examination, and a second group of RF coils, which are configured to receive MR signals from the object undergoing examination. Furthermore, the MR apparatus has at least one RF coil that is configured to emit a pilot tone (PT) navigator signal. The PT method, and the associated PT generators and PT signal emitters, are described in more detail in the documents cited above.

The magnetic resonance apparatus 1 furthermore has an MR control computer 13 that controls the MR apparatus 1. The central MR control computer 13, which is configured so as to implement the method described below for performing electrical impedance tomography (EIT), has a gradient controller 14 for controlling and switching the magnetic resonance gradients, and an RF controller 15 for controlling and radiating the RF pulses for the purpose of deflecting the nuclear spins from the equilibrium position, and for emitting the continuous RF signals. The imaging sequences that are needed for capturing the MR images and the EIT images may be stored, for example, in a memory 16, as may also all the programs needed for operating the MR apparatus 1 and for performing electrical impedance tomography according to the method according to the invention. A sequence controller 17 controls image capture and hence, dependent on the selected imaging sequences, controls the sequence of magnetic field gradients and RF pulses, the receiving intervals of MR signals, and the emission and receiving of the continuous RF signals. In this way, the sequence controller 17 also controls the gradient controller 14 and the RF controller 15. Thus, simultaneously with the MR method, the sequence controller 17 also controls the EIT method and hence also the RF coils that are used to emit continuous RF signals and the RF coils that are used to receive the modulated continuous RF signals.

A reconstruction computer 20 calculates MR images and EIT images, which can be displayed on a display 18. A person operating the MR apparatus 1 can enter operating commands via an input unit 19. The memory 16 can have imaging sequences and program modules stored therein that, when they are executed in the control computer 13 and/or sequence controller 17 and/or the reconstruction computer 20, perform the method according to the invention for electrical impedance tomography, as explained in detail below. For this purpose, the memory 16 stores control information that can be executed by the MR control computer 13 and the other components noted above. In particular, the sequence controller 17 is thereby configured to perform the method described below for performing electrical impedance tomography (EIT).

Hardware and software features that are present in the MR apparatus 1 are utilized to perform EIT/RFIM using the MRI scanner, as described below.

According to the invention, the MR apparatus 1 in FIG. 1 is operated such that, when the control information is executed in the MR control computer 13, the basic magnetic field is produced in which a person undergoing examination 12 is situated. Furthermore, nuclear spins are excited in the person undergoing examination by an RF pulse while the basic magnetic field is applied. Furthermore, MR signals from the person undergoing examination are detected. Simultaneously, continuous RF signals having amplitudes in the same order of magnitude as the amplitudes of the received MR signals are emitted into the tunnel of the scanner 10 by at least one RF coil.

During this procedure, the EIT method is referenced to the pilot tone (PT) navigation framework described above. It is known from the Master's thesis "Informationsgehalt eines neuartigen MR-Navigators in Bezug auf physiologische Vorgänge [*Information content of a novel MR navigator relating to physiological procedures*]" by Lea Schröder, Friedrich-Alexander-Universitat Erlangen-Nürnberg, 2015 that the PT navigator has a sensitive response to multidimensional respiratory motion, cardiac contraction and movements of the extremities. Moreover, this document also describes how the volume of motion that contributes to modulation of the PT signal is approximately constrained by the distance between the emitter and the receiver.

FIG. 2 is a flowchart with steps for performing a method for performing electrical impedance tomography (EIT) according to an exemplary embodiment of the invention.

The method begins at step S1. In step S2, an RF pulse is emitted by a first group of RF coils 2 for the purpose of exciting certain nuclear spins in the object undergoing examination 12. In step S3, MR signals are received from the object undergoing examination 12 on the basis of the RF pulse, by a second group of RF coils 2. Here, the MR imaging supplies exact modeling boundaries: body geometry, tissue distribution (e.g. distribution of soft tissue/cavity/fat, content of fat/water per voxel, separation of organs by segmentation and/or user inputs, fiber orientation from DTI), dynamic parameters (such as cardiac contraction, respiratory deformation).

In step S4, continuous RF signals, which have amplitudes in the same order of magnitude as the amplitudes of the MR signals, are emitted by at least one RF coil 2. The frequency or frequencies of the continuous RF signals are selected such that the resonance condition for exciting nuclear spins in the object undergoing examination 12 does not occur, and so nuclear spins are not excited in the object undergoing examination 12, and the excitation of nuclear spins is not affected by the RF pulse. The amplitudes here are selected to be small enough to lie in the range of the MR signals and thus prevent the MR imaging from being affected by the continuous RF signals. Here, the currents are not supplied to the body, or the object undergoing examination 12, through a galvanic contact but over an air gap of a pilot tone emitter, as a single-frequency signal of constant amplitude.

The RF signals have a negligible effect on the spin dynamic as a result of the small-amplitude currents that are required in order to remain within the high-signal-fidelity, unsaturated range of the MR receivers, and their narrow frequency content, which avoids the resonance condition. As a result, the EIT method according to the invention can be performed simultaneously—that is to say independently of the MR measurement—without adapting the MR measurement.

In step S5, modulated continuous RF signals are received from the object undergoing examination 12 in response to the continuous RF signals, by the second group of RF coils 2. In particular, the continuous RF signals undergo a modulation by the object undergoing examination 12, in particular a modulation of the phase and/or a modulation of the amplitude, as a result of which the modulated continuous RF signals are generated by interaction with the object undergoing examination 12. Here, currents are received over an air gap with the MR local receiving coils, and are detected in the MR receivers with phase coherence.

The bandwidth of the MR signals at the time of excitation corresponds approximately to the bandwidth of the excitation pulse. However, the RF signals are only measured when the MR apparatus 1 is ready to receive—that is to say between the excitation pulses, in particular during the periods in which the MR signals are received from the object undergoing examination 12. During the receiving period, the bandwidth of the MR signals is determined by applied BO coding gradients. It may be greater than or smaller than the bandwidth of the excitation pulse. Typical values for the bandwidth of the excitation pulse are 1 kHz for the MR excitation pulse and 250 kHz for the MR signal.

For the MR measurement, the sequence of excitation with an RF pulse and the receiving of MR signals is separated in time. This is not the case for the continuous RF signals. Here, at one point in time the continuous RF signal applying at this point in time is detected. Because the MR system is only ready to receive between the excitation pulses, the continuous RF signals can be emitted throughout the entire MR measurement procedure, i.e., during emission of the RF pulse and receiving of the MR signals. It is also possible, however, to restrict the generation of the continuous RF signals only to those periods when the MR system is ready to receive.

The emission of the continuous RF signals in step S4 and the receiving of the modulated continuous RF signals in step S5 are performed simultaneously with the receiving of MR signals in step S3. In this arrangement, the MR imaging can also deliver information on changing boundary conditions in real time during the EIT measurement.

As a result, the MR and the EIT measurement methods are performed simultaneously and independently of one another, and the MR data and EIT measurement data can be evaluated at the same time in the MR system. As a result, the measurement data and the evaluated data of both the measurement methods can be used in the respectively other method to enhance the accuracy of the imaging method.

In step S6, an image of the object undergoing examination 12 is determined, based on the modulated continuous RF signals. In particular, the modulated continuous RF signals are used to determine image data on which the image of the object undergoing examination is based. In this way, the modulated continuous RF signals are evaluated such that an image of the object undergoing examination from an EIT technique is generated from the image data of the continuous RF signals. Here, model inversion is performed with the use of MR image reconstruction hardware, which can be integrated into the MR image reconstruction software. In particular, the modeling boundaries determined in step S3 can be used to perform the EIT method more accurately and more quickly. The method ends at step S7.

The following conclusions can be drawn from the exemplary embodiments described above:

In an exemplary embodiment, EIT images can be represented using the standard MR system software in an additional step of the method.

In another exemplary embodiment, pilot tone emitters that are not integrated into the MR coils can be placed in positions that are optimal for EIT of a particular organ.

In another exemplary embodiment, a number of pilot tone emitters can be placed in different positions, in order to enhance the information in the EIT measurement and to stabilize model inversion. The signal contributions from the individual emitters may differ in respect of their frequency, the direction of their electromagnetic polarization, and any signal modulation, and may be differentiated by these properties in the data received.

In another exemplary embodiment having a number of emitters operated in parallel, a series of emitters at the same frequency may be activated sequentially, or one emitter may be shifted in space in order to increase the quantity of data.

In another exemplary embodiment, the object undergoing examination 12 is not static but has a known dynamic modulating its electrical properties. In this way, the problem of inversion can be simplified in that only the variation in the measurement with the dynamic is considered, wherein static portions of the model are omitted. For example, the EIT measurement may be carried out with temporal resolution using the heartbeat, and only the difference in the signals between the systolic and the diastolic values is evaluated, on the assumption that the dynamic is restricted to the heart, or using MR information with temporal resolution. The same applies to respiratory motion or pulsatile blood flow in the tissue.

In another exemplary embodiment, EIT-based tissue characterization may be used for medical purposes. By using frequencies close to the Larmor frequency in the scanner, such as MR-RFIM, an additional use is possible: EIT results can then be used for the patient-specific modeling of B1 in order to support steps taken to optimize MRI, such as SAR calculations or PTx adaptations.

In summary, a method for performing electrical impedance tomography (EIT) using an MR system is provided, wherein continuous RF signals for EIT are emitted simultaneously with the receiving of the MR signals using at least one RF coil, and continuous RF signals that are modulated by the object undergoing examination are received by the MR coils. An image of the object undergoing examination is determined on the basis of the modulated continuous RF signals using an EIT technique. In an exemplary embodiment, by avoiding the resonant frequencies and by using a single-frequency continuous RF signal of small, constant amplitude, the possibility that the EIT method will interact with the MR method is eliminated.

The method according to the invention enables improved EIT imaging to be provided on an MR system with integrated pilot tone navigation simultaneously with the MR imaging. The close connection with MR imaging enhances the quality of the EIT results, and in particular allows EIT to be performed without additional patient preparation in parallel with the MR measurement. In this way, a more accurate provision for patients at lower cost than in conventional EIT examination methods is provided.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for performing electrical impedance tomography (EIT) on an object undergoing examination using a magnetic resonance apparatus comprising a plurality of radio-frequency (RF) coils, said method comprising:
    radiating an RF pulse using a first group of said RF coils that excites nuclear spins in the object undergoing examination;
    receiving MR signals from the object undergoing examination produced as a result of the RF pulse, with a second group of said RF coils;
    simultaneously with receiving of the MR signals, radiating continuous RF signals having amplitudes in a same order of magnitude as amplitudes of the MR signals, from at least one RF coil in said plurality of RF coils;
    also simultaneously with receiving of the MR signals, receiving modulated continuous RF signals from the object undergoing examination in response to the continuous RF signals, with the second group of said RF coils; and
    reconstructing an EIT image of the object undergoing examination based on the modulated continuous RF signals.

2. The method as claimed in claim 1, comprising radiating said continuous RF signals in a frequency range that does not produce a resonance condition for exciting nuclear spin in the object undergoing examination.

3. The method as claimed in claim 1, comprising radiating said continuous RF signals in a frequency range that is outside a frequency range of the MR signals from the object undergoing examination and that is within a frequency receiving range of the second group of RF coils.

4. The method as claimed in claim 1, comprising radiating said continuous RF signals as a single-frequency RF signal of constant amplitude.

5. The method as claimed in claim 1, comprising from the at least one RF coil that radiates the continuous RF signals, also radiating a pilot tone navigator signal.

6. The method as claimed in claim 1, wherein the at least one RF coil that radiates the continuous RF signals is in the second group of RF coils.

7. The method as claimed in claim 1, wherein the at least one RF coil that radiates the continuous RF signals is not in the second group of RF coils, and is situated closer to the object undergoing examination than RF coils in the second group of RF coils.

8. The method as claimed in claim 1, comprising reconstructing said EIT image of the object undergoing examination using a phase of the modulated continuous RF signals, which is an absolute phase is determined in relation to the emitted RF signals, or a relative phase change in the modulated continuous RF signals over time.

9. The method as claimed in claim 1, comprising reconstructing said EIT image of the object undergoing examination additionally using the received MR signals.

10. The method as claimed in claim 1 further comprising:
    determining a frequency range of the received MR signals from the object undergoing examination; and
    radiating the continuous RF signals outside the determined frequency range of the MR signals.

11. The method as claimed in claim 1, comprising radiating the continuous RF signals from a plurality of RF coils.

12. The method as claimed in claim 11, comprising radiating the continuous RF signals from the plurality of RF coils simultaneously, with the continuous RF signals of the individual RF coils respectively differing as to at least one emission property, selected from the group consisting of frequency, relative phase, amplitude, direction of electromagnetic polarization, and signal modulation.

13. The method as claimed in claim 11, comprising radiating the continuous RF signals from plurality of RF coils sequentially.

14. The method as claimed in claim 13, comprising radiating the continuous RF signals from the plurality of RF coils simultaneously, with the continuous RF signals of the individual RF coils respectively differing as to at least one emission property, selected from the group consisting of frequency, relative phase, amplitude, direction of electromagnetic polarization, and signal modulation.

15. The method as claimed in claim 14, comprising sequentially varying said at least one emission property.

16. The method as claimed in claim 11, wherein at least one of the RF coils is shifted in space.

17. The method as claimed in claim 1, wherein the object undergoing examination undergoes a dynamic change, and comprising reconstructing said EIT image of the object using only variations in the continuous modulated RF signals that occur due to the dynamic change.

18. The method as claimed in claim 1, wherein the amplitudes of the continuous RF signals are substantially a same size as the amplitudes of the MR signals.

19. A magnetic resonance (MR) apparatus for performing electrical impedance tomography (EIT) on an object undergoing examination, said MR apparatus comprising:
    an MR data acquisition scanner comprising a plurality of radio-frequency RF coils, in which said object undergoing examination is situated;
    a computer configured to operate said MR data acquisition scanner so as to radiate an RF pulse using a first group of said RF coils that excites nuclear spins in the object undergoing examination;
    said computer being configured to operate said MR data acquisition scanner so as to receive MR signals from the object undergoing examination produced as a result of the RF pulse, with a second group of said RF coils;
    said computer being configured to operate said MR data acquisition scanner so as to, simultaneously with receiving of the MR signals, radiating continuous RF signals having amplitudes in a same order of magnitude as amplitudes of the MR signals, from at least one RF coil in said plurality of RF coils;
    said computer being configured to operate said MR data acquisition scanner so as to, also simultaneously with receiving of the MR signals, receiving modulated continuous RF signals from the object undergoing examination in response to the continuous RF signals, with the second group of said RF coils; and
    said computer being configured to operate said MR data acquisition scanner so as to reconstruct an EIT image of the object undergoing examination based on the modulated continuous RF signals.

20. A non-transitory, computer-readable data storage medium encoded with programming instructions, said storage medium being loaded into a computer of a magnetic resonance (MR) apparatus, comprising an MR data acquisition scanner with a plurality of radio-frequency (RF) coils, in which an object undergoing examination is situated for electrical impedance tomography (EIT), said programming instructions causing said computer to:
    operate the MR data acquisition scanner so as to radiate an RF pulse using a first group of said RF coils that excites nuclear spins in the object undergoing examination;
    operate the MR data acquisition scanner so as to receive MR signals from the object undergoing examination produced as a result of the RF pulse, with a second group of said RF coils;
    operate the MR data acquisition scanner so as to, simultaneously with receiving of the MR signals, radiating continuous RF signals having amplitudes in a same order of magnitude as amplitudes of the MR signals, from at least one RF coil in said plurality of RF coils;
    operate the MR data acquisition scanner so as to, also simultaneously with receiving of the MR signals, receiving modulated continuous RF signals from the object undergoing examination in response to the continuous RF signals, with the second group of said RF coils; and
    operate the MR data acquisition scanner so as to reconstruct an EIT image of the object undergoing examination based on the modulated continuous RF signals.

* * * * *